(12) United States Patent
Pacetti

(10) Patent No.: US 7,786,249 B2
(45) Date of Patent: *Aug. 31, 2010

(54) BIOBENEFICIAL POLYAMIDE/POLYETHYLENE GLYCOL POLYMERS FOR USE WITH DRUG ELUTING STENTS

(75) Inventor: Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 12/207,424

(22) Filed: Sep. 9, 2008

(65) Prior Publication Data

US 2009/0012243 A1 Jan. 8, 2009

Related U.S. Application Data

(62) Division of application No. 10/741,214, filed on Dec. 19, 2003, now Pat. No. 7,435,788.

(51) Int. Cl.
*C08G 69/40* (2006.01)
*C08G 69/44* (2006.01)

(52) U.S. Cl. .................. 528/288; 424/423; 528/291; 528/292; 528/300; 528/308.6; 528/335; 528/340

(58) Field of Classification Search ............... 424/423; 528/291, 292, 300, 308.6, 335, 340
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 3,773,737 A | 11/1973 | Goodman et al. | |
| 3,849,514 A | 11/1974 | Gray, Jr. et al. | |
| 4,226,243 A | 10/1980 | Shalaby et al. | |
| 4,304,767 A | 12/1981 | Heller et al. | |
| 4,329,383 A | 5/1982 | Joh | |
| 4,343,931 A | 8/1982 | Barrows | |
| 4,368,090 A | 1/1983 | Mumcu et al. | |
| 4,483,975 A | 11/1984 | De Jong et al. | |
| 4,529,792 A | 7/1985 | Barrows | |
| 4,611,051 A | 9/1986 | Hayes et al. | |
| 4,656,242 A | 4/1987 | Swan et al. | |
| 4,733,665 A | 3/1988 | Palmaz | |
| 4,800,882 A | 1/1989 | Gianturco | |
| 4,882,168 A | 11/1989 | Casey et al. | |
| 4,886,062 A | 12/1989 | Wiktor | |
| 4,931,287 A | 6/1990 | Bae et al. | |
| 4,941,870 A | 7/1990 | Okada et al. | |
| 4,977,901 A | 12/1990 | Ofstead | |
| 5,019,096 A | 5/1991 | Fox, Jr. et al. | |
| 5,100,992 A | 3/1992 | Cohn et al. | |
| 5,112,457 A | 5/1992 | Marchant | |
| 5,133,742 A | 7/1992 | Pinchuk | |
| 5,163,952 A | 11/1992 | Froix | |
| 5,165,919 A | 11/1992 | Sasaki et al. | |
| 5,219,980 A | 6/1993 | Swidler | |
| 5,258,020 A | 11/1993 | Froix | |
| 5,272,012 A | 12/1993 | Opolski | |
| 5,292,516 A | 3/1994 | Viegas et al. | |
| 5,298,260 A | 3/1994 | Viegas et al. | |
| 5,300,295 A | 4/1994 | Viegas et al. | |
| 5,306,501 A | 4/1994 | Viegas et al. | |
| 5,306,786 A | 4/1994 | Moens et al. | |
| 5,328,471 A | 7/1994 | Slepian | |
| 5,330,768 A | 7/1994 | Park et al. | |
| 5,380,299 A | 1/1995 | Fearnot et al. | |
| 5,417,981 A | 5/1995 | Endo et al. | |
| 5,447,724 A | 9/1995 | Helmus et al. | |
| 5,455,040 A | 10/1995 | Marchant | |
| 5,462,990 A | 10/1995 | Hubbell et al. | |
| 5,464,650 A | 11/1995 | Berg et al. | |
| 5,485,496 A | 1/1996 | Lee et al. | |

(Continued)

FOREIGN PATENT DOCUMENTS

DE 196 52 037 6/1998

(Continued)

OTHER PUBLICATIONS

Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).

(Continued)

*Primary Examiner*—Ana L Woodward
(74) *Attorney, Agent, or Firm*—Squire Sanders & Dempsey, LLP

(57) ABSTRACT

This disclosure covers polymers, which are useful in medical device applications. The polymers comprise at least two different blocks, at least one L1 block with the formula

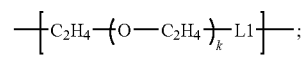

and at least one L2 block with the formula

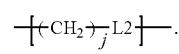

Medical devices comprising these polymers, mixtures of these polymers with therapeutic agents, and methods of making these polymers and mixtures are within the scope of this disclosure. Some of these medical devices are implantable within a mammalian body, such as in a body lumen.

21 Claims, No Drawings

U.S. PATENT DOCUMENTS

| | | |
|---|---|---|
| 5,489,667 A | 2/1996 | Knipf et al. |
| 5,516,881 A | 5/1996 | Lee et al. |
| 5,569,463 A | 10/1996 | Helmus et al. |
| 5,578,073 A | 11/1996 | Haimovich et al. |
| 5,581,387 A | 12/1996 | Cahill |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,837,802 A | 11/1998 | Van Lith et al. |
| 5,849,859 A | 12/1998 | Acemoglu |
| 5,851,508 A | 12/1998 | Greff et al. |
| 5,854,376 A | 12/1998 | Higashi |
| 5,858,746 A | 1/1999 | Hubbell et al. |
| 5,861,387 A | 1/1999 | Labrie et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,273,913 B1 | 8/2001 | Wright et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,316,585 B1 | 11/2001 | Lele et al. |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,381 B1 | 4/2002 | Hossainy et al. |
| 6,383,215 B1 | 5/2002 | Sass |
| 6,387,379 B1 | 5/2002 | Goldberg et al. |
| 6,395,326 B1 | 5/2002 | Castro et al. |
| 6,419,692 B1 | 7/2002 | Yang et al. |
| 6,420,045 B1 | 7/2002 | Faulhammer et al. |
| 6,451,373 B1 | 9/2002 | Hossainy et al. |
| 6,475,779 B2 | 11/2002 | Mathiowitz et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |

| | | | | | | |
|---|---|---|---|---|---|---|
| 6,530,951 B1 | 3/2003 | Bates et al. | | 7,261,735 B2 | 8/2007 | Llanos et al. |
| 6,540,776 B2 | 4/2003 | Sanders Millare et al. | | 7,290,933 B2 | 11/2007 | Braun et al. |
| 6,544,223 B1 | 4/2003 | Kokish | | 7,323,210 B2 | 1/2008 | Castro et al. |
| 6,544,543 B1 | 4/2003 | Mandrusov et al. | | 7,384,660 B2 | 6/2008 | Hossainy et al. |
| 6,544,582 B1 | 4/2003 | Yoe | | 7,390,333 B2 | 6/2008 | Dutta |
| 6,555,157 B1 | 4/2003 | Hossainy | | 7,390,523 B2 | 6/2008 | Pacetti et al. |
| 6,558,733 B1 | 5/2003 | Hossainy et al. | | 7,402,329 B2 | 7/2008 | Pacetti et al. |
| 6,565,659 B1 | 5/2003 | Pacetti et al. | | 7,435,788 B2 | 10/2008 | Pacetti |
| 6,572,644 B1 | 6/2003 | Moein | | 7,470,283 B2 | 12/2008 | Dutta |
| 6,585,765 B1 | 7/2003 | Hossainy et al. | | 2001/0007083 A1 | 7/2001 | Roorda |
| 6,585,926 B1 | 7/2003 | Mirzaee | | 2001/0029351 A1 | 10/2001 | Falotico et al. |
| 6,600,010 B2 | 7/2003 | Mao et al. | | 2001/0037145 A1 | 11/2001 | Guruwaiya et al. |
| 6,605,154 B1 | 8/2003 | Villareal | | 2002/0005206 A1 | 1/2002 | Falotico et al. |
| 6,613,084 B2 | 9/2003 | Yang | | 2002/0007213 A1 | 1/2002 | Falotico et al. |
| 6,613,432 B2 | 9/2003 | Zamora et al. | | 2002/0007214 A1 | 1/2002 | Falotico |
| 6,616,765 B1 | 9/2003 | Castro et al. | | 2002/0007215 A1 | 1/2002 | Falotico et al. |
| 6,620,617 B2 | 9/2003 | Mathiowitz et al. | | 2002/0051730 A1 | 5/2002 | Bodnar et al. |
| 6,623,448 B2 | 9/2003 | Slater | | 2002/0077693 A1 | 6/2002 | Barclay et al. |
| 6,625,486 B2 | 9/2003 | Lundkvist et al. | | 2002/0082679 A1 | 6/2002 | Sirhan et al. |
| 6,641,611 B2 | 11/2003 | Jayaraman | | 2002/0087123 A1 | 7/2002 | Hossainy et al. |
| 6,645,135 B1 | 11/2003 | Bhat | | 2002/0091433 A1 | 7/2002 | Ding et al. |
| 6,645,195 B1 | 11/2003 | Bhat et al. | | 2002/0111590 A1 | 8/2002 | Davila et al. |
| 6,656,216 B1 | 12/2003 | Hossainy et al. | | 2002/0176849 A1 | 11/2002 | Slepian |
| 6,656,506 B1 | 12/2003 | Wu et al. | | 2002/0183581 A1 | 12/2002 | Yoe et al. |
| 6,660,034 B1 | 12/2003 | Mandrusov et al. | | 2002/0188037 A1 | 12/2002 | Chudzik et al. |
| 6,663,662 B2 | 12/2003 | Pacetti et al. | | 2002/0188277 A1 | 12/2002 | Roorda et al. |
| 6,663,880 B1 | 12/2003 | Roorda et al. | | 2003/0004141 A1 | 1/2003 | Brown |
| 6,666,880 B1 | 12/2003 | Chiu et al. | | 2003/0028243 A1 | 2/2003 | Bates et al. |
| 6,673,154 B1 | 1/2004 | Pacetti et al. | | 2003/0028244 A1 | 2/2003 | Bates et al. |
| 6,673,385 B1 | 1/2004 | Ding et al. | | 2003/0032767 A1 | 2/2003 | Tada et al. |
| 6,689,099 B2 | 2/2004 | Mirzaee | | 2003/0036794 A1 | 2/2003 | Ragheb et al. |
| 6,689,350 B2 | 2/2004 | Uhrich | | 2003/0039689 A1 | 2/2003 | Chen et al. |
| 6,695,920 B1 | 2/2004 | Pacetti et al. | | 2003/0040790 A1 | 2/2003 | Furst |
| 6,703,040 B2 | 3/2004 | Katsarava et al. | | 2003/0059520 A1 | 3/2003 | Chen et al. |
| 6,706,013 B1 | 3/2004 | Bhat et al. | | 2003/0065377 A1 | 4/2003 | Davila et al. |
| 6,709,514 B1 | 3/2004 | Hossainy | | 2003/0072868 A1 | 4/2003 | Harish et al. |
| 6,712,845 B2 | 3/2004 | Hossainy | | 2003/0073961 A1 | 4/2003 | Happ |
| 6,713,119 B2 | 3/2004 | Hossainy et al. | | 2003/0083739 A1 | 5/2003 | Cafferata |
| 6,716,444 B1 | 4/2004 | Castro et al. | | 2003/0097088 A1 | 5/2003 | Pacetti |
| 6,723,120 B2 | 4/2004 | Yan | | 2004/0029952 A1 | 2/2004 | Chen et al. |
| 6,730,064 B2 | 5/2004 | Ragheb et al. | | 2004/0052858 A1 | 3/2004 | Wu et al. |
| 6,733,768 B2 | 5/2004 | Hossainy et al. | | 2004/0052859 A1 | 3/2004 | Wu et al. |
| 6,740,040 B1 | 5/2004 | Mandrusov et al. | | 2004/0054104 A1 | 3/2004 | Pacetti |
| 6,743,462 B1 | 6/2004 | Pacetti | | 2004/0060508 A1 | 4/2004 | Pacetti et al. |
| 6,746,773 B2 | 6/2004 | Llanos et al. | | 2004/0063805 A1 | 4/2004 | Pacetti et al. |
| 6,749,626 B1 | 6/2004 | Bhat et al. | | 2004/0071861 A1 | 4/2004 | Mandrusov et al. |
| 6,753,071 B1 | 6/2004 | Pacetti et al. | | 2004/0073298 A1 | 4/2004 | Hossainy |
| 6,758,859 B1 | 7/2004 | Dang et al. | | 2004/0096504 A1 | 5/2004 | Michal |
| 6,759,054 B2 | 7/2004 | Chen et al. | | 2005/0106204 A1 | 5/2005 | Hossainy et al. |
| 6,764,505 B1 | 7/2004 | Hossainy et al. | | 2005/0112171 A1 | 5/2005 | Tang et al. |
| 6,776,796 B2 | 8/2004 | Falotico et al. | | 2005/0208091 A1 | 9/2005 | Pacetti |
| 6,780,424 B2 | 8/2004 | Claude | | 2005/0208093 A1 | 9/2005 | Glauser et al. |
| 6,790,228 B2 | 9/2004 | Hossainy et al. | | 2005/0245637 A1 | 11/2005 | Hossainy et al. |
| 6,824,559 B2 | 11/2004 | Michal | | 2005/0265960 A1 | 12/2005 | Pacetti |
| 6,860,946 B2 | 3/2005 | Hossainy et al. | | 2005/0271700 A1 | 12/2005 | DesNoyer et al. |
| 6,887,510 B2 | 5/2005 | Villareal | | 2005/0287184 A1 | 12/2005 | Hossainy et al. |
| 6,890,583 B2 | 5/2005 | Chudzik et al. | | | | |
| 6,908,624 B2 | 6/2005 | Hossainy et al. | | FOREIGN PATENT DOCUMENTS | | |
| 6,955,723 B2 | 10/2005 | Pacetti et al. | | | | |
| 6,986,899 B2 | 1/2006 | Hossainy et al. | | EP | 0 301 856 | 2/1989 |
| 6,991,681 B2 | 1/2006 | Yoe | | EP | 0 396 429 | 11/1990 |
| 7,008,667 B2 | 3/2006 | Chudzik et al. | | EP | 0 451 951 | 10/1991 |
| 7,014,861 B2 | 3/2006 | Roorda et al. | | EP | 0 451 954 | 10/1991 |
| 7,056,591 B1 | 6/2006 | Pacetti et al. | | EP | 0 514 406 | 11/1992 |
| 7,077,859 B2 | 7/2006 | Sirhan et al. | | EP | 0 583 888 | 2/1994 |
| 7,087,263 B2 | 8/2006 | Hossainy et al. | | EP | 0 604 022 | 6/1994 |
| 7,115,299 B2 | 10/2006 | Kokish | | EP | 0 623 354 | 11/1994 |
| 7,150,738 B2 | 12/2006 | Ray et al. | | EP | 0 665 023 | 8/1995 |
| 7,169,173 B2 | 1/2007 | Hossainy et al. | | EP | 0 701 802 | 3/1996 |
| 7,195,640 B2 | 3/2007 | Falotico et al. | | EP | 0 716 836 | 6/1996 |
| 7,220,816 B2 | 5/2007 | Pacetti et al. | | EP | 0 809 999 | 12/1997 |
| 7,241,832 B2 | 7/2007 | Khemani et al. | | EP | 0 832 655 | 4/1998 |
| 7,258,891 B2 | 8/2007 | Pacetti et al. | | EP | 0 850 651 | 7/1998 |

| | | |
|---|---|---|
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| GB | 1 137 209 | 12/1968 |
| JP | 2001-190687 | 7/2001 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/03218 | 1/1998 |
| WO | WO 98/08463 | 3/1998 |
| WO | WO 98/17331 | 4/1998 |
| WO | WO 98/32398 | 7/1998 |
| WO | WO 98/32777 | 7/1998 |
| WO | WO 98/36784 | 8/1998 |
| WO | WO 99/01118 | 1/1999 |
| WO | WO 99/13924 | 3/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/56376 | 9/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/39810 | 6/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/26281 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/017892 | 3/2004 |
| WO | WO 2004/101018 | 11/2004 |
| WO | WO 2005/011770 | 2/2005 |
| WO | WO 2005/039489 | 5/2005 |
| WO | WO 2005/042600 | 5/2005 |
| WO | WO 2005/051445 | 6/2005 |
| WO | WO 2005/061024 | 7/2005 |
| WO | WO 2005/066241 | 7/2005 |

OTHER PUBLICATIONS

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Nordrehaug et al., *A novel biocompatible coating applied to coronary stents*, European Heart Journal 14, p. 321 (p. 1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, Vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Scully et al., *Effect of a heparan sulphate with high affinity for antithrombin III upon inactivation of thrombin and coagulaton Factor Xa*, Biochem J. 262, (1989) pp. 651-658.

Shigeno, *Prevention of Cerebrovascular Spasm by Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

BIOBENEFICIAL POLYAMIDE/POLYETHYLENE GLYCOL POLYMERS FOR USE WITH DRUG ELUTING STENTS

CROSS-REFERENCE TO RELATED APPLICATION

This is a divisional application of U.S. application Ser. No. 10/741,214, filed Dec. 19, 2003 now U.S. Pat. No. 7,435,788, the teaching of which is incorporated herein in its entirety by reference.

BACKGROUND

Percutaneous transluminal coronary angioplasty (PTCA) is a procedure for treating heart disease. A surgeon introduces a catheter assembly having a balloon portion percutaneously into the cardiovascular system of a patient via the brachial or femoral artery. The surgeon advances the catheter assembly through the coronary vasculature until the balloon portion crosses the occlusive lesion. Once in position, the surgeon inflates the balloon to radially compress the atherosclerotic plaque of the lesion and remodel the vessel wall. The surgeon then deflates the balloon to remove the catheter.

But this procedure can create intimal flaps or tear arterial linings, which can collapse and occlude the vessel after balloon removal. Moreover, thrombosis and restenosis of the artery may develop over several months following the procedure, which may require another angioplasty procedure or a by-pass operation. To reduce artery occlusion, thrombosis, and restenosis, the surgeon can implant a stent into the vessel.

Stents are used not only mechanically, but also to provide biological therapy. Mechanically, stents act as scaffoldings, physically holding open and, if desired, expanding the vessel wall. Typically, stents compress for insertion through small vessels and then expand to a larger diameter once in position. U.S. Pat. No. 4,733,665, issued to Palmaz; U.S. Pat. No. 4,800,882, issued to Gianturco; and U.S. Pat. No. 4,886,062, issued to Wiktor disclose examples of PTCA stents.

Medicating the stent provides for pharmacological therapy. Medicated stents allow local drug administration at the diseased site. To provide an effective drug concentration at the treated site, systemic treatment often requires concentrations that produce adverse or toxic effects. Local delivery advantageously allows for smaller systemic drug levels in comparison to systemic treatment. Because of this, local delivery produces fewer side effects and achieves more favorable results. One proposed method for medicating stents involves coating a polymeric carrier onto a stent surface. This method applies a solution that includes a solvent, a dissolved polymer, and a dissolved or dispersed drug to the stent. As the solvent evaporates, it leaves a drug impregnated, polymer coating on the stent.

Current biomaterials research aims at controlling protein adsorption on implantable medical devices. Current biomaterials exhibit uncontrolled protein adsorption, leading to a mixed layer of partially denatured proteins. Current surfaces contain different cell binding sites resulting from adsorbed proteins such as fibrinogen and immunoglobulin G. Platelets and inflammatory cells such as macrophages and neutrophils adhere to these surfaces. When so activated, these cells secret a wide variety of pro-inflammatory and proliferative factors. Non-fouling surfaces control these events. Thus surfaces absorb little or no protein, primarily due to their hydrophilicity. One prior art approach creates these surfaces by using hyaluronic acid and polyethylene glycol. Non-fouling surfaces or coatings are a subset of biobeneficial coatings. Biobeneficial coatings benefit the treatment site without releasing pharmaceutically or therapeutically active agents, ("drug(s)"). Another type of biobeneficial coating contains free-radical scavengers, which preserve nitric oxide and prevent oxidative damage.

SUMMARY

This invention relates to biobeneficial copolymers, which are useful in medical device applications. Such medical devices are implantable within a mammalian body, such as in a body lumen or blood vessel. For purposes of this disclosure, the term "biobeneficial" is a description for any surface that bestows biological benefit to an implantable medical device without releasing drug(s). The copolymers comprise at least two different blocks, at least one L1 block with the formula shown in Formula I, below

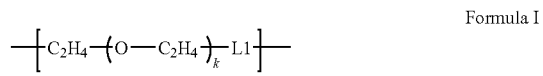

Formula I and at least one L2 block with the formula shown in Formula II, below

Formula II

More generally, the L1 block can be as shown in Formula III, below.

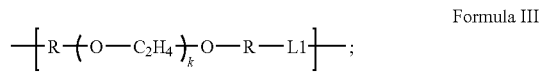

Formula III

The L1 blocks are the same or different. R are the same or different for each occurrence and are 1-16 carbon (un)substituted, (un)branched alkyl or (un)substituted, (un)branched diol or triol oligomers. And k are the same or different for each L1 block ranging from 6 to 460. Similarly, the L2 blocks are the same or different, and j are the same or different for each L2 block ranging from 2 to 30. Some embodiments select R to be the same; some embodiments select Rs to be different. Exemplary R include oligomers of ethylene glycol, propylene glycol (1,2- and 1,3-substituted isomers), tetramethylene glycol (1,2-, 1,3-, 1,4-, and 2,3-substituted isomers), and hexamethylene glycol (1,2-, 1,3-, 1,4-1,5-, 1,6-, 2,3-, 2,4-, 2,5-, 3,4-substituted isomers). One of ordinary skill in the art recognizes that any of the preceding glycols will yield unbranched moieties when substituted at the first and last carbon atom and will yield branched moieties with other substitutions patterns. Some embodiments are envisioned that use mixtures of polyols. In addition to polyol oligomers, R can be (un)branched alkyl, alkenyl, or alkynyl moieties. In many instances throughout the disclosure the R-group is specified as an ethylene or ethylene glycol unit. When this occurs, the formula is intended to represent its genus with an R-groups as defined in this paragraph and is intended to represent the species with the specified R-group shown. Also, as a point of clarity, the above L1 block is written below in Formula IV with R defined as it would be if the polyether portion of the L1 block were selected to be PEG and the L1 portion is a diamide.

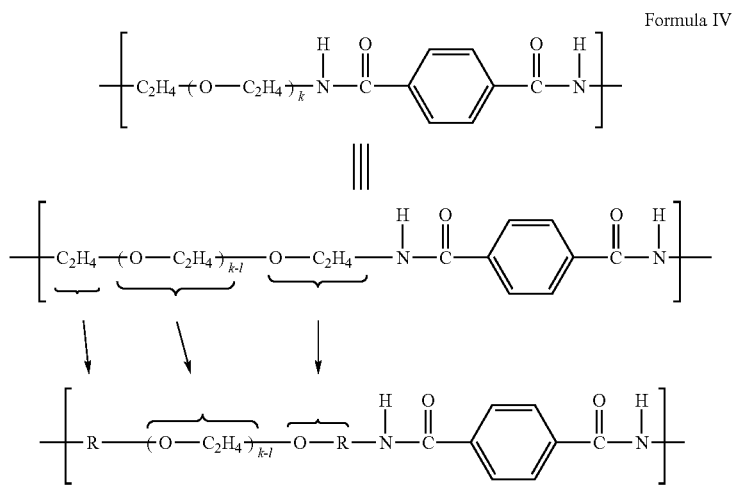

Formula IV

L1 and L2, independently, represent linkages with the formula shown in Formula V, above.

Formula V

In this formula, Y and Z are independently selected from the moieties shown in Structure Table I, below.

STRUCTURE TABLE I

| | | | | Formula VI |
|---|---|---|---|---|
| ●−C(=O)−O− | ester | ●−O−C(=O)−N(H)− | urethane |
| ●−C(=O)−N(H)− | amide | ●−O− | ether |
| ●−N(H)−C(=O)−O− | urethane | ●−O−C(=O)−O− | carbonate |
| ●−N(H)−C(=O)−N(H)− | urea | ●−C(=O)−S− | thioester | provided that if Y and Z are the same, they are not

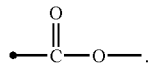

In the above list, the heavy circle indicates the position at which Y or Z attaches to the phenyl ring of L1 or L2, respectively.

In some embodiments, these polymers compose structural polymeric medical devices and compose coatings for polymeric, metallic, ceramic, glass, or composite medical devices. In addition to this, these polymers can be mixed with other polymers, with drugs, or with both. Methods of making medical devices using these polymers are disclosed, as well.

DETAILED DESCRIPTION

This disclosure reveals a family of biobeneficial, polyamide-polyethylene-glycol polymers. In some embodiments, these polymers compose the base material for implantable medical devices. In some embodiments, implantable medical devices comprise these polymers. And in some embodiments, these polymers compose implantable medical device coatings. This polymer family comprises the reaction products of various reactants, wherein reactants comprise the following basic components: terephthalic acid (Formula VII, below) or a similar 1,4-difunctionally substituted benzyl group, amine-terminated polyethylene glycol or another group, as described below, and at least one aliphatic diamine. Throughout this disclosure, 1,4-disubstituted phenyl or benzyl rings are referred to or depicted. For this disclosure, such reference or depiction includes variations in which the phenyl or benzyl rings are additionally substituted at least at the 2, 3, 5, or 6 positions. Any substitution is allowed.

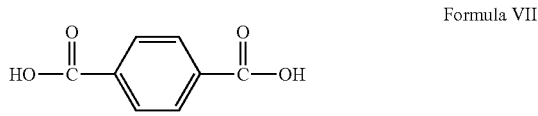

Formula VII

Invention embodiments contain amine-terminated polyethylene glycol, such as the ED series of Jeffamine polymers (from Huntsman Chemical) or mono-amine-terminated PEG (from Shearwater Polymers). These Jeffamine polymers have a polyethylene glycol backbone with some polypropylene glycol units at the chain ends. The polypropylene units contain the primary amine.

Invention embodiments contain an aliphatic diamine, such as 1,2-ethanediamine (Formula VIII, below),

Formula VIII or 1,4-butanediamine (Formula IX, below),

Formula IX

Both of these diamines are biocompatible in the unlikely event that in-vivo use causes their release. The synthesis of invention polymers is straightforward using standard nylon polymerization techniques. Other useful diamines are 1,5-pentanediamine, 1,6-heaxanediamine, and 1,6-diaminocyclohexane. Embodiments that have branching from the diamine backbone are within the scope of this description. In some embodiments, the diamine is selected from straight chain or branched, aliphatic diamino compounds where the amino groups are primary or secondary and the total number of carbons per diamine is 16 or less.

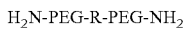

Formula X

In Formula X, R can be polyethylene, polypropylene, polyisobutylene, polyisoprene, polybutene, poly(hexamethylene glycol), poly(tetramethylene glycol), or poly(propylene glycol), and R has a molecular weight of 26 to 500 Daltons. Some embodiments can be described as having an optional linkage between the R and the PEG. This linkage could be any of those shown in Structure Table I, above.

Some invention embodiments select the amine-terminated polyethylene glycol, or the aliphatic diamines, or both, to be primary amines. One of ordinary skill in the art recognizes that similar chemistry would arise from using secondary amines for the amine-terminated polyethylene glycol or the aliphatic diamines. This disclosure defines a linkage prepared using secondary amines as a "substituted amide linkage" shown in Formula XI, below:

Formula XI

Some invention embodiments select the amine-terminated polyethylene glycol or the aliphatic diamines or both to be secondary amines. On the other hand, some invention embodiments specifically exclude secondary amines from being the amine-terminated polyethylene glycol or the aliphatic diamines or both. Likewise, some invention embodiments exclude primary amines from being the amine-terminated polyethylene glycol or the aliphatic diamines or both.

For polymers that contain bioabsorbable components, the biobeneficial component should also be bioabsorbable. Similarly, for polymers containing biostable components, such as EVAL, the biobeneficial component would ideally be biostable, as well. This is because the biobeneficial feature has both acute and chronic, long-term effects. PEG, for example, works by resisting protein adhesion and denaturation at the implant surface.

This disclosure reveals, among other embodiments, a biostable version of a polyester, biodegradable copolymer POLYACTIVE in which at least some replacement of the ester linkages by amide (or other) linkages occurs. POLYACTIVE is a trade name of a PBT-PEG group of products and is available from IsoTis Corp. of Holland. In various brands of POLYACTIVE, the molar ratio between the units derived from ethylene glycol and the units derived from butylene terephthalate falls between about 0.01:1 and about 1:1. The molecular weight of the units derived from ethylene glycol can be between about 300 and about 10,000 Daltons. The structure of POLYACTIVE is shown in Formula XII, below.

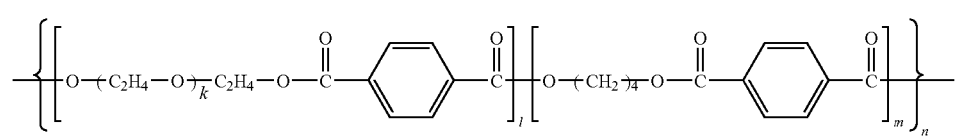

Formula XII

For POLYACTIVE, k ranges from 4 to 230, or more narrowly, from 7 to 91. The values of l, m, and n constrain each other for a given molecular weight. Therefore, the value of m is set to unity and the values of l and n will give the ratio of the two blocks and the total molecular weight. l ranges from 0.003 to 0.60, or more narrowly, from 0.01 to 0.45. And n ranges from 30 to 500, or more narrowly, from 100 to 375.

Replacing ester linkages with amide linkages yields Formula XIII, below:

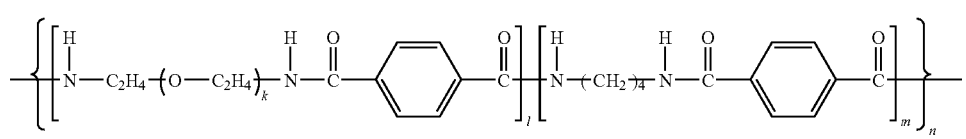

Formula XIII

For invention polymers, k ranges from 4 to 230, or more narrowly, from 7 to 91. l ranges from 0.005 to 2.0, or more narrowly, from 0.01 to 1.6. m is set at unity. And n ranges from 20 to 600, or more narrowly, from 40 to 450.

In some embodiments, amide linkages replace all ester linkages in POLYACTIVE. Alternatively, in some embodiments, amide linkages replace 25-100 percent of the ester linkages; amide linkages replace 50-100 percent of the ester linkage; amide linkages replace 75-100 percent of the ester linkages; amide linkages replace 95-100 percent of the ester linkages; or amide linkages replace 99-100 percent of the ester linkages. Alternatively, in some embodiments 25-100 percent of the ester linkages remain after some amide linkage replacement; 50-100 percent of the ester linkage remain after some amide linkage replacement; 75-100 percent of the ester linkages remain after some amide linkage replacement; 95-100 percent of the ester linkages remain after some amide linkage replacement; or 99-100 percent of the ester linkages remain after some amide linkage replacement.

This amide substitution removes the ester linkage from POLYACTIVE or reduces the number of ester linkages compared with the number in POLYACTIVE. Ester linkages hydrolyze in-vivo. But amide linkages are many times more stable. Some invention embodiments select the polymer formulation such that the resulting polymer is substantially broken down by the in vivo environment in an amount of time of from 1 to 24 months; alternatively, in an amount of time of from 2 to 18 months; alternatively, in an amount of time of from 3 to 12 months. For purposes of this disclosure, substantially broken down means that non-invasive diagnostic procedures as skilled artisans normally employ cannot detect the polymer in vivo.

For some embodiments, biocompatible means that the material passes or is found acceptable by at least one of the following in vitro tests, as specified by ISO 10993. These in vitro tests would include ISO 10993-5 cytotoxicity (this is a L929 mouse fibroblast test using extracts of the material); ISO 10993-4 hemocompatibility (this is a specific test for thrombosis, coagulation, platelet consumption, hematology, and immunology); ISO 10993-3 genotoxicity (this includes the Ames test, mouse cell lymphoma test, and Chinese hamster ovary cell test).

In some embodiments, invention polymers comprise at least one L1 block, shown in Formula III, above and at least one L2 block, shown in Formula II, above. In these invention polymers, the L1 blocks are the same or different and k are the same or different for each L1 block and range from 6 to 460. Likewise, the L2 blocks are the same or different and j are the same or different for each L2 block and range from 2 to 30.

Formula XIV, Formula XV and Formula XVA, below, represent some invention embodiments.

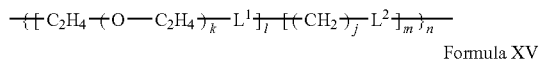
Formula XIV

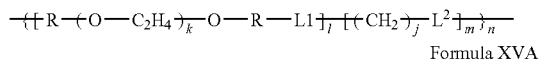
Formula XV

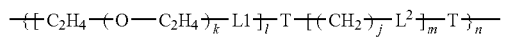
Formula XVA

Where, in Formula XVA,
a) L1 is a linkage with the following formula

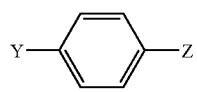

wherein Y and Z are independently selected from the following moieties

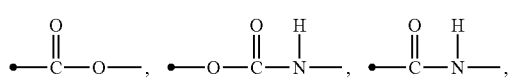

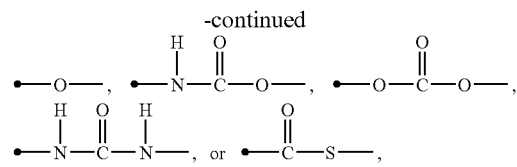

provided that if Y and Z are the same, they are not

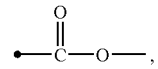

and
wherein the symbol "●" indicates the position at which Y or Z attaches to the phenyl ring of L1;
b) L2 is a linkage with the following formula

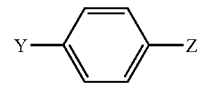

wherein Y and Z are independently selected from the following moieties

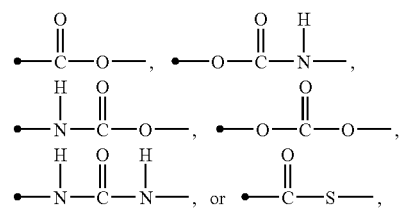

provided that if Y and Z are the same, they are not

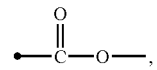

and
wherein the symbol "●" indicates the position at which Y or Z attaches to the phenyl ring of L2,
c) T represents the same or different biocompatible polymeric or non-polymeric linkage comprising from 1-100 atoms;
d) j ranges from 2 to 30;
e) k ranges from 6 to 460;
f) l ranges from 0.005 to 2.0;
g) m is 1;
h) n ranges from 20 to 600;
i) the weight average molecular weight of the polymer ranges from 38,000 to 188,000 Daltons.

In some embodiments, T is at least one of polyethylene, polypropylene, polyisobutylene, polyisoprene, polybutene, poly(hexamethylene glycol), poly(tetramethylene glycol), or poly(propylene glycol). In some embodiments, T has a molecular weight of 26 to 500 Daltons. In some embodiments, T connects into the polymer with one or more of the following linkages:

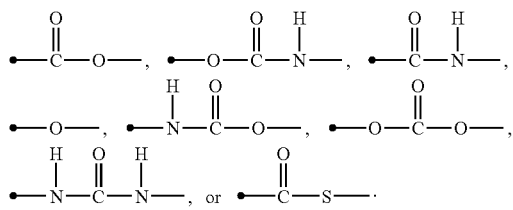

For these embodiment, k, l, m, n, take the above-disclosed values. m equals one, leaving l to define the ratio of l to m and n to define to total molecular weight. j ranges from 2 to 30, or more narrowly, from 2 to 6.

L1 and L2 independently have Formula V, as shown above. Some embodiments independently select L1 and L2, as indicated above. In other embodiments, L1 and L2 are purposely chosen to be the same. Other embodiments purposely choose L1 and L2 to be different from each other. In any of these embodiments, appropriate selection of Y and Z yields Y and Z that are both more resistant to in vivo hydrolysis than an ester moiety, appropriate selection of Y and Z yields Y and Z in which one or the other is more resistant to in vivo hydrolysis than an ester moiety, or appropriate selection of Y and Z yields Y and Z that are both less resistant to in vivo hydrolysis than an ester moiety. One of ordinary skill in the art recognizes that if a secondary amine were chosen above, any amides selected for Y or Z would be substituted amides. Some invention embodiments specifically exclude Y or Z equal to one of or any combination of esters, amides, urethanes, ureas, ethers, carbonates, or thioesters, or corresponding substituted amides.

Structure Table II, below, shows non-inclusive examples of L1 and L2:

contain polymers that are branched or cross-linked, partially cross-linked, or not cross-linked, as desired. In some embodiments, invention polymers have less than 0.1 mole percent of branched polymers in which the branches have more than 10 atoms; alternatively, invention polymers have less than 0.01 mole percent of such branched polymers; alternatively, invention polymers have less than 0.001 mole percent of such branched polymers. In some embodiments, invention polymers have greater than 0.1 mole percent of branched polymers in which the branches have more than 10 atoms; alternatively, invention polymers have greater than 0.01 mole percent of such branched polymers; alternatively, invention polymers have greater than 0.001 mole percent of such branched polymers. In some embodiments, invention polymers have less than 0.1 mole percent of cross-linked polymers; alternatively, invention polymers have less than 0.01 mole percent of cross-linked polymers; alternatively, invention polymers have less than 0.001 mole percent of cross-linked polymers. In some embodiments, invention polymers have greater than 0.1 mole percent of cross-linked polymers; alternatively, invention polymers have greater than 0.01 mole percent of cross-linked polymers; alternatively, invention polymers have greater than 0.001 mole percent of cross-linked polymers. Partially cross-linked means having greater than 0.001 mole percent and less than 0.1 mole percent of cross-linked polymers.

In some instances, cross-linking occurs through functional groups pendant from the polymer backbone. For instance, in some embodiments urethanes or amides in the backbone can serve as the cross-linking site, via the use of diisocyanates. Those of ordinary skill in the art will recognize that other ways of achieving cross-links between polymer chains function with invention copolymers. For example, to UV crosslink the polymers, some embodiments may have UV polymerizable groups in the monomers. Such groups are typically acry-

STRUCTURE TABLE II

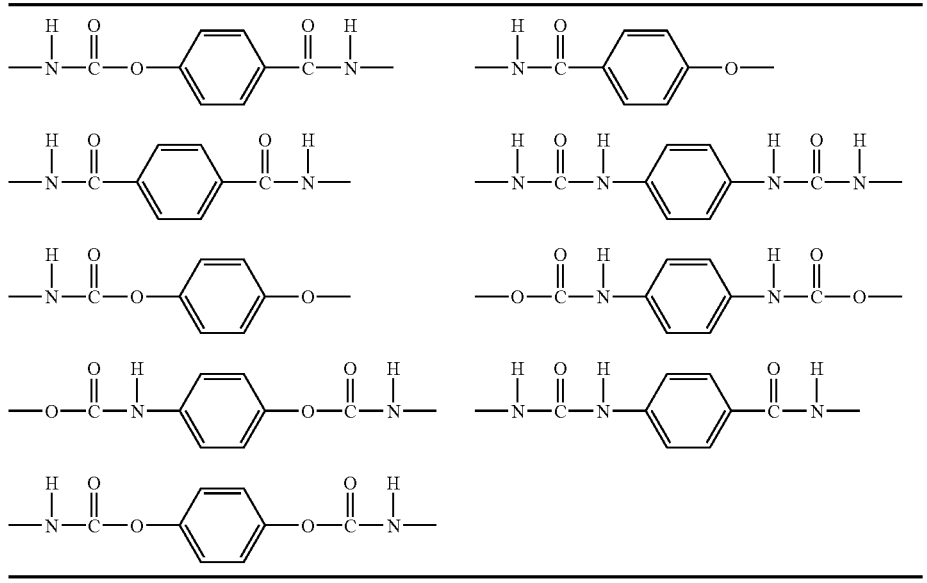

Some invention embodiments specifically exclude L1 and L2 from being any one or any combination of the moieties listed above in Structure Table II, above.

Some invention embodiments comprise linear polymers, some exclusively so. But various invention embodiments can lates or methacrylates. One general scheme would include placing acrylate or methacrylate groups onto the phenyl groups after the condensation polymerization. In another scheme, the acrylate or methacrylate groups would be present on the PEG based-diamine, aliphatic diamine, or the difunctional phenyl moiety (e.g., terephthalic acid). This scheme is workable if the condensation reactions are selective enough not to react with the acrylate or methacrylate groups. This gives rise to another class of polymers.

Some embodiments comprise invention polymers coated onto a medical device containing or constructed from a polymer, a medical device containing or constructed from a metal, or a bare medical device, or invention polymers coated on top of a drug coating already present on a medical device. Alternatively, some embodiments comprise invention polymers disposed between a medical device and a drug coating. Also, some embodiments comprise invention polymers composing polymer-based medical devices or invention polymers composing medical device substrates (implantable or not). Some invention embodiments comprise medical devices not made from polymer-containing or -constructed stents. Some invention embodiments comprise stents not made from metal-containing or constructed stents.

In some embodiments, invention polymers serve as the base material for coatings on medical devices. In some embodiments, coatings may contain a primer layer composed of an invention polymer or composed of a type-two polymer, as described below. Some embodiments exclude a primer layer.

Some embodiments add conventional drugs, such as small, hydrophobic drugs, to invention polymers (as discussed in any of the embodiments, above), making them biostable, drug systems. Some embodiments graft on conventional drugs or mix conventional drugs with invention polymers. Invention polymers can be coated as blends with a variety of biobeneficial polymers. Moreover, they can serve as base or topcoat layers for biobeneficial polymer layers.

The selected drug can inhibit vascular, smooth muscle cell activity. More specifically, the drug activity can aim at inhibiting abnormal or inappropriate migration or proliferation of smooth muscle cells to prevent, inhibit, reduce, or treat restenosis. The drug can also include any substance capable of exerting a therapeutic or prophylactic effect in the practice of the present invention. Examples of such active agents include antiproliferative, antineoplastic, antiinflammatory, antiplatelet, anticoagulant, antifibrin, antithrombin, antimitotic, antibiotic, and antioxidant substances as well as their combinations. An example of an antiproliferative substance is actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Examples of antineoplastics include paclitaxel and docetaxel. Examples of antiplatelets, anticoagulants, antifibrins, and antithrombins include aspirin, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocor). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen), angiotensin converting enzyme inhibitors such as CAPTOPRIL (available from Squibb), CILAZAPRIL (available from Hoffinan-LaRoche), or LISINOPRIL (available from Merck & Co., Whitehouse Station, N.J.), calcium channel blockers (such as Nifedipine), colchicine, fibroblast growth factor (FGF) antagonists, histamine antagonist, LOVASTATIN (an inhibitor of HMG-CoA reductase, a cholesterol lowering drug from Merck &Co.), monoclonal antibodies (such as PDGF receptors), nitroprusside, phosphodiesterase inhibitors, prostaglandin inhibitor (available from Glazo), Seramin (a PDGF antagonist), serotonin blockers, thioprotease inhibitors, triazolopyrimidine (a PDGF antagonist), and nitric oxide. Other useful drugs may include alpha-interferon, genetically engineered epithelial cells, dexamethasone, estradiol, clobetasol propionate, cisplatin, insulin sensitizers, receptor tyrosine kinase inhibitors, and carboplatin. Exposure of the composition to the drug should not adversely alter the drug's composition or characteristic. Accordingly, drug-containing embodiments choose drugs that are compatible with the blended composition. Rapamycin is a suitable drug. Additionally, 40-O-(2-hydroxy)ethyl-rapamycin, or a functional analog or structural derivative thereof, is suitable, as well. Examples of analogs or derivatives of 40-O-(2-hydroxy)ethyl-rapamycin include, among others, 40-O-(3-hydroxy)propyl-rapamycin and 40-O-2-(2-hydroxy)ethoxyethyl-rapamycin. Those of ordinary skill in the art know of various methods and coatings for advantageously controlling the release rate of drugs, such as 40-O-(2-hydroxy)ethyl-rapamycin.

Some embodiments choose the drug such that it does not contain at least one of or any combination of antiproliferative, antineoplastic, antiinflammatory, antiplatelet, anticoagulant, antifibrin, antithrombin, antimitotic, antibiotic, or antioxidant substances. Some invention embodiments choose the drug such that it does not contain at least one of or any combination of actinomycin D, derivatives and analogs of Actinomycin D, dactinomycin, actinomycin IV, actinomycin $I_1$, actinomycin $X_1$, actinomycin $C_1$, paclitaxel, docetaxel, aspirin, sodium heparin, low molecular weight heparin, hirudin, argatroban, forskolin, vapiprost, prostacyclin, prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor and 7E-3B, methotrexate, azathioprine, vincristine, vinblastine, fluorouracil, adriamycin, mutamycin, angiopeptin, angiotensin converting enzyme inhibitors, CAPTOPRIL, CILAZAPRIL, or LISINOPRIL, calcium channel blockers, Nifedipine, colchicine, fibroblast growth factor (FGF) antagonists, histamine antagonist, LOVASTATIN, monoclonal antibodies, PDGF receptors, nitroprusside, phosphodiesterase inhibitors, prostaglandin inhibitor, Seramin, PDGF antagonists, serotonin blockers, thioprotease inhibitors, triazolopyrimidine, nitric oxide, alpha-interferon, genetically engineered epithelial cells, dexamethasone, estradiol, clobetasol propionate, cisplatin, insulin sensitizers, receptor tyrosine kinase inhibitors, carboplatin, Rapamycin, 40-O-(2-hydroxy)ethyl-rapamycin, or a functional analogs of 40-O-(2-hydroxy)ethyl-rapamycin, structural derivative of 40-O-(2-hydroxy)ethyl-rapamycin, 40-O-(3-hydroxy)propyl-rapamycin, and 40-O-2-(2-hydroxy)ethoxyethyl-rapamycin.

Some invention embodiments comprise a drug or drug combination, and some require a drug or combination of drugs. Of the drugs specifically listed above, some invention embodiments exclude a single or any combination of these drugs.

These blends could also be formulated to modulate or tune the release rate of drugs from coatings, reservoirs, or particles composed of these blends and drugs or therapeutic agents. Blends with other polymers can be formulated to modulate the mechanical properties of invention polymers. Therefore, some invention embodiments comprise polymer blends with other polymeric components. For purposes of this disclosure, these other polymeric components are sometimes referred to as type-two polymers. For instance, type-two polymers could be blended into invention polymers to modify mechanical or biological properties or vice versa. Type-two polymers include, among others, polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(3-hydroxybutyrate-co-3-hydroxyvalerate), poly(tyrosine derived carbonates), poly(tyrosine arylates), poly(imino carbonates), poly(trimethylene carbonate), poly(anhydrides), poly(orthoesters), and poly(ester amides) or combinations of these polymers. In some embodiments, polymer blends with invention polymers do not contain at least one of polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derived carbonates), poly(tyrosine arylates), poly(imino carbonates), poly(trimethylene carbonate), poly(anhydrides), poly(orthoesters), or poly(ester amides).

Type-two polymers also include ethylene vinyl alcohol copolymer, poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; poly(ester-urethanes); poly(ether-urethanes); poly(urea-urethanes); poly(silicone-urethanes); polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; poly(vinylidene fluoride-co-hexafluoropropene), poly(vinylidene fluoride-co-chlorotrifluoropropene); polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

Some invention embodiments comprise, and some invention embodiments require, a type-two polymer used along with invention polymers. Some invention embodiments comprise and some invention embodiments require combining at least two type-two polymers with invention polymers. Of the type-two polymers disclosed above, some invention embodiments exclude a single or any combination of type-two polymers.

In some embodiments in which invention polymers are used with type-two polymers, the invention polymers are mixed or blended with the type-two polymers.

For example, some embodiments comprise invention polymers physically blended with PEG, POLYACTIVE, or other biobeneficial polymers. Additionally, some embodiments employ invention polymers blended with biobeneficial polymers and type-two polymers.

For purposes of this disclosure, "modulate biological outcome" means adjusting the polymer biobeneficial-component content in order to minimize fibrinogen absorption, platelet binding, the number of adherent macrophages and inflammatory cells, and the degree of inflammatory cell activation.

Some embodiments comprise invention polymers combined with other polymers in multilayer arrangements. For example, an invention polymer could under- or over-lay another polymer such as a polymer coated on a device, a medical device, an implantable medical device, or a stent. The invention polymer can be used neat in this regard, or it can first B mixed with a separate invention polymer or a type-two polymer before layering. In some embodiments, invention polymers do not underlay another polymer; in other embodiments, invention polymers must overlay another polymer.

Examples of implantable devices useful in the present invention include self-expandable stents, balloon-expandable stents, stent-grafts, grafts (e.g., aortic grafts), vascular grafts, artificial heart valves, cerebrospinal fluid shunts, pacemaker electrodes, guidewires, ventricular assist devices, artificial hearts, cardiopulmonary by-pass circuits, blood oxygenators, and endocardial leads (e.g., FINELINE and ENDOTAK, available from Guidant Corporation, Santa Clara, Calif.). The underlying structure of the device can be of virtually any design. The device can comprise a metallic material or an alloy such as, but not limited to, cobalt chromium alloy (EL-GILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium, and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Some invention embodiments define the genre of medical devices to exclude at least one of self-expandable stents, balloon-expandable stents, stent-grafts, grafts (e.g., aortic grafts), vascular grafts, artificial heart valves, cerebrospinal fluid shunts, pacemaker electrodes, guidewires, ventricular assist devices, artificial hearts, cardiopulmonary by-pass circuits, blood oxygenators, or endocardial leads.

A coating for an implantable medical device, such as a stent, according to embodiments of the present invention, can be a multi-layer structure that can include the following three layers:
 (a) an optional primer layer;
 (b) a drug-polymer layer (also referred to as "reservoir" or "reservoir layer") or alternatively a polymer-free drug layer; and/or
 (c) an optional topcoat layer, which is likewise drug-containing or drug-free.

Some invention embodiments comprise multilayered structures in which an invention polymer is present in one or more of the layers of the multilayered structure.

In some embodiments, forming each medical device coating layer comprises dissolving the polymer or a polymer blend in a solvent or a solvent mixture, and applying the solution onto the medical device (such as by spraying the medical device with the solution or by dipping the medical device into the solution). After applying the solution onto the medical device, the coating dries by solvent evaporation. Drying at elevated temperatures accelerates the process.

Combining the drug with the polymer solution, as described above, provides for incorporating the drug into the reservoir layer. Alternatively, dissolving the drug in a suitable solvent or solvent mixture and applying the drug solution to the medical device provides for a substantially polymer-free drug layer.

Instead of introducing the drug as a solution, the drug can be introduced as a colloid, such as a suspension in a solvent. Dispersing the drug in the solvent uses conventional techniques. Depending on a variety of factors, e.g., the nature of the drug, those having ordinary skill in the art can select the solvent for the suspension, as well as the quantity of the dispersed drug. Some embodiments mix these suspensions with a polymer solution and apply the mixture onto the device, as described above. Alternatively, some embodiments apply the drug suspension to the device without mixing it with the polymer solution.

The drug-polymer layer can be applied directly onto at least a part of the medical device surface to serve as a reservoir for at least one active agent or a drug. The optional primer layer can be applied between the device and the reservoir to improve polymer adhesion to the medical device. Some embodiments apply the topcoat layer over at least a portion of the reservoir layer, and the topcoat layer serves as a rate limiting membrane, which helps to control the rate of release of the drug.

Some drug releasing processes include at least two steps. First, the topcoat polymer absorbs the drug at the drug-polymer-topcoat interface. Next, the drug diffuses through the topcoat using empty spaces between the polymer molecules as diffusion pathways. Next, the drug arrives to the outer surface of the topcoat, and desorbs into the blood stream.

Invention polymers can be prepared by polycondensation reactions. First, the amine-terminated PEG is combined with terephthaloyl chloride with added pyridine to absorb the released HCl. After this block has reacted, the aliphatic diamine is added with additional teraphthaloyl chloride. Irganox 1330 can be added as an antioxidant to protect the PEG, as it is used in the synthesis of POLYACTIVE. Routes that use dimethyl terephthalate would avoid using the acid chloride. Application of heat and vacuum to remove the generated methanol will drive the polymerization.

Of course, modifications to this synthesis must be made when L1 or L2 are not prepared to contain amide linkages, i.e. when L1 and L2 do not have the structure shown below. Such modifications are well within the skill level of one of ordinary skill in the art.

By making the PEG block large enough, and the copolymer random enough to keep the hard blocks small, the solubility can be adjusted.

EXAMPLE SYNTHESIS

Prophetic Example 1

Synthesis of
PEG-terephthalamide/butylene-terephthalamide
block copoly(ether amide)

To a 500 ml, three necked round bottom flask equipped with nitrogen inlet, vacuum line, and mechanical stirrer is added Jeffamine ED-600 (37.36 g, 0.0623 moles) (shown below in Formula XVI). The flask is heated to 40° C. and a vacuum of less than 10 torr is drawn for 2 hours to remove any moisture. Nitrogen is introduced and the flask is cooled to room temperature. 125 ml of dry dimethyforrnamide is added with triethylamine (26 g, 0.257 moles), and 1,4-butanediamine (34.86 g, 0.172 moles). Terephthaloyl chloride (47.51 g, 0.234 moles) is slowly added to the reaction vessel and the solution slowly heated to 60° C. and allowed to react for 4 hours. After cooling, slow addition of the reaction mixture into 2 liters of stirred, deionized water will cause precipitation of the polymer, the formula of which is shown below in Formula XVII.

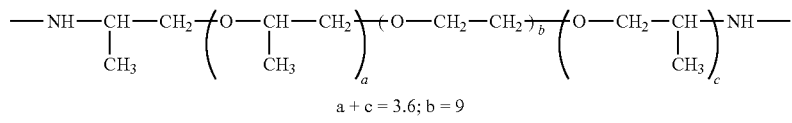

Formula XVI

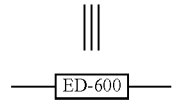

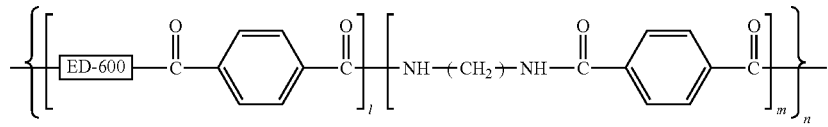

Formula XVII

Prophetic Example 2

Synthesis of PEG-terephthalamideurethane/butylene-terephthalamideurethane block copoly(ether amide urethane)

To a 500 ml, three necked round bottom flask equipped with nitrogen inlet, vacuum line, and mechanical stirrer is added Jeffamine ED-2003 (36.67 g, 0.0183 moles) (shown below in Formula XVIII). The flask is heated to 60° C. and a vacuum of less than 10 torr is drawn for 2 hours to remove any moisture. Nitrogen is introduced and the flask is cooled to room temperature. Pyridine (20.88 g, 0.264 moles) is added, and 4-isocyanatobenzoyl chloride (43.64 g, 0.24 moles) is slowly added in a solution of 125 ml of dry dimethylformamide. The solution slowly heated to 60° C. and allowed to react for 4 hours. 1,4-butanediamine (19.61 g, 0.222 moles) is added and allowed to react at 60° C. for another 4 hours. After cooling, slow addition of the reaction mixture into 2 liters of stirred deionized water will cause precipitation of the polymer, which is shown below in Formulas Formula XIX-Formula XXII. Each of the Formulas Formula XIX-Formula XXII represent the same polymer, the only difference in the orientations of the benzoyl-derived group. For purposes of this disclosure listing one of formulas Formula XIX-Formula XXII represents each of Formula XIX-Formula XXII.

wherein a) L1 is a linkage with the following formula

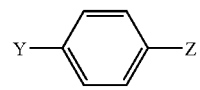

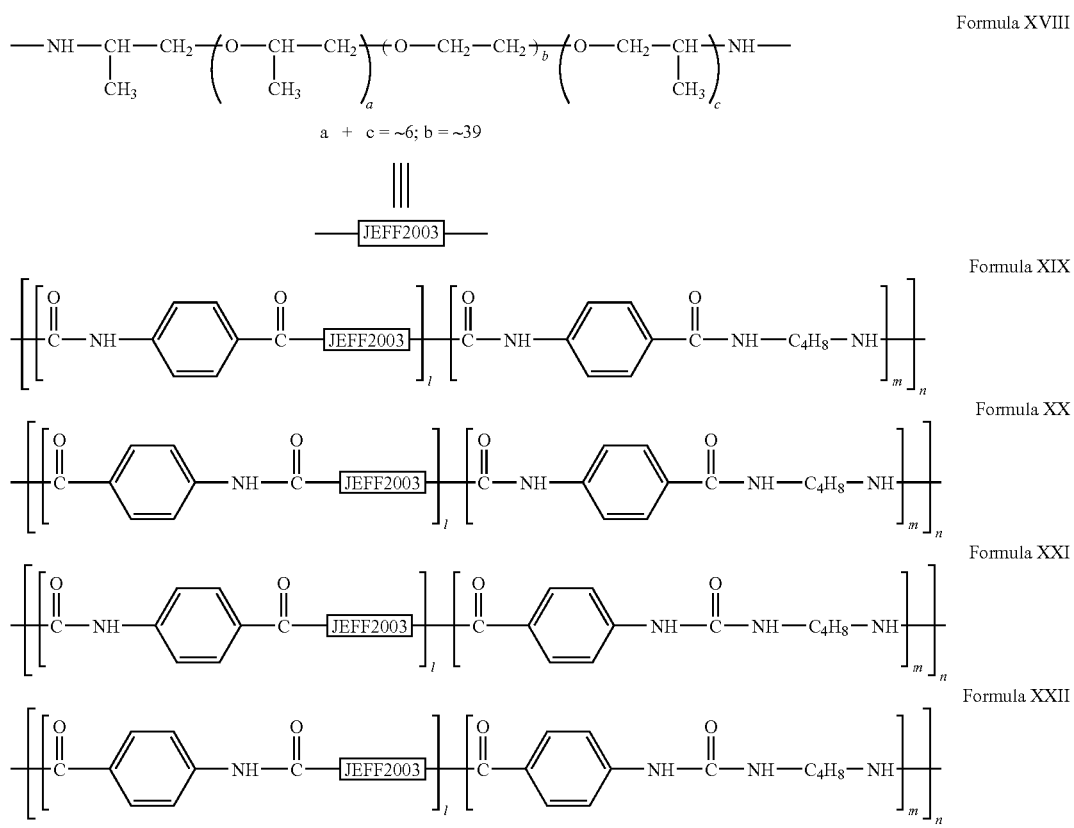

Formula XVIII

Formula XIX

Formula XX

Formula XXI

Formula XXII

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention.

What is claimed is:

1. A polymer comprising at least one of L1 blocks and at least one of L2 blocks, having the following formula

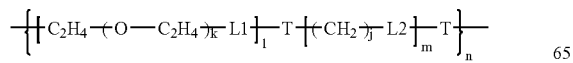

wherein Y and Z are independently selected from the following moieties

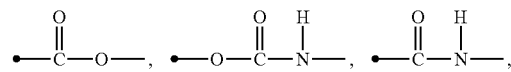

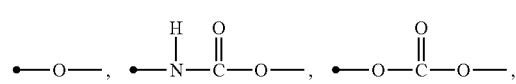

provided that if Y and Z are the same, they are not

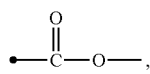

and
 wherein the symbol "•" indicates the position at which Y or Z attaches to the phenyl ring of L1;
 b) L2 is a linkage with the following formula

wherein Y and Z are independently selected from the following moieties

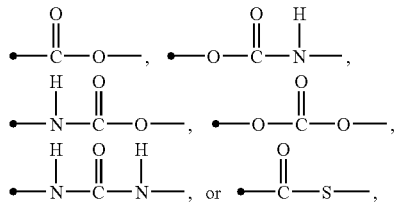

provided that if Y and Z are the same, they are not

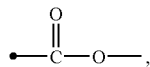

and
 wherein the symbol "•" indicates the position at which Y or Z attaches to the phenyl ring of L2,
 c) T represents the same or different biocompatible polymeric or non-polymeric linkage comprising from 1-100 atoms;
 d) j ranges from 2 to 30;
 e) k ranges from 6 to 460;
 f) l ranges from 0.005 to 2.0;
 g) m is 1;
 h) n ranges from 20 to 600;
 i) the weight average molecular weight of the polymer ranges from 38,000 to 188,000 Daltons.

2. The polymer of claim 1 wherein T is at least one of polyethylene, polypropylene, polyisobutylene, polyisoprene, polybutene, poly(hexamethylene glycol), poly(tetramethylene glycol), or poly(propylene glycol).

3. The polymer of claim 2 wherein T has a molecular weight of 26 to 500 Daltons.

4. The polymer of claim 3 wherein T connects into the polymer with one or more of the following linkages

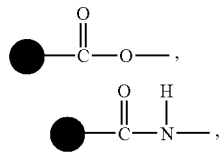

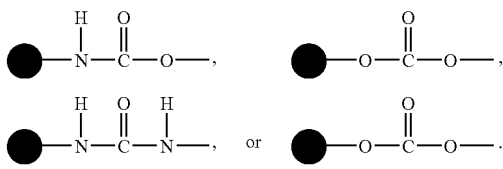

5. The polymer of claim 1 wherein Y and Z of L1 or L2 are independently selected from

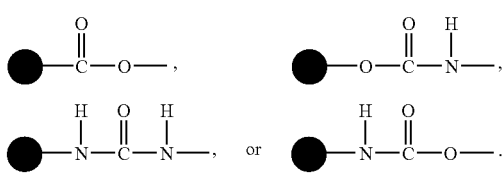

6. The polymer of claim 1 wherein Y and Z are independently selected from

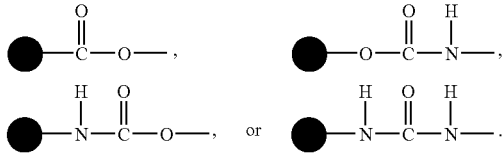

7. The polymer of claim 1 wherein L1 and L2 are independently selected from any of the following linking groups

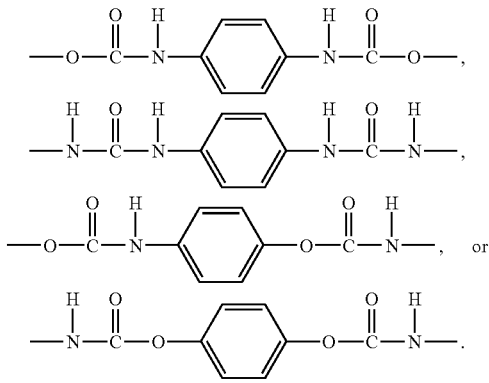

8. The polymer of claim 1 wherein L1 and L2 are selected from any of the following linking groups

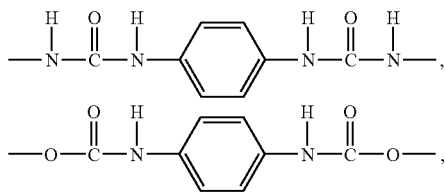

-continued

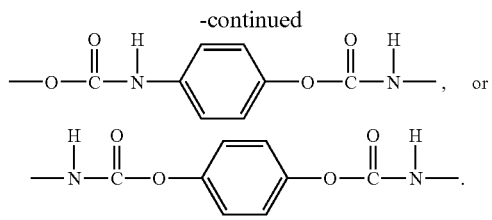

9. The polymer of claim 8 wherein L1 and L2 are the same.

10. The polymer of claim 1 wherein Y and Z of L1 are esters, amides, urethanes, ureas, ethers, carbonates, or thioesters, provided that both Y and Z are not esters.

11. The polymer of claim 1 wherein Y and Z of L1 are amides, urethanes, ureas, ethers, or carbonates.

12. The polymer of claim 1 wherein Y and Z of L1 are amides, urethanes, or ureas.

13. The polymer of claim 1 wherein 0-75% of Y and Z of L1 and L2 combined are

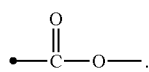

14. The polymer of claim 1 wherein 0-50% of Y and Z of L1 and L2 combined are

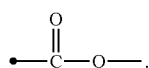

15. The polymer of claim 1 wherein 0-25% of Y and Z of L1 and L2 combined are

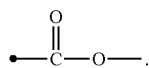

16. The polymer of claim 1 wherein 0-5% of Y and Z of L1 and L2 combined are

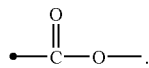

17. The polymer of claim 1 wherein 90-99% of Y and Z of L1 and L2 combined are

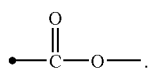

18. The polymer of claim 1 wherein 75-100% of Y and Z of L1 and L2 combined are

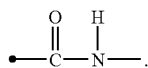

19. The polymer of claim 1 wherein 50-100% of Y and Z of L1 and L2 combined are

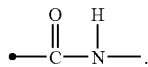

20. The polymer of claim 1 wherein
a) L1 blocks have the following formula

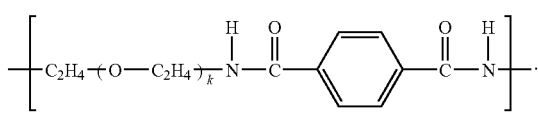

21. The polymer of claim 1 wherein
L2 blocks have one of the following formulas

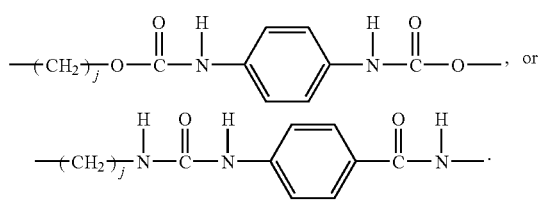

* * * * *